(12) United States Patent
Moniz

(10) Patent No.: US 6,282,987 B1
(45) Date of Patent: Sep. 4, 2001

(54) CONTACT BAR ASSEMBLY FOR A TATTOOING DEVICE

(76) Inventor: John G. Moniz, 62 Friendly Rd., Cranston, RI (US) 02910

( * ) Notice: Subject to any disclaimer, the term of this patent is extended or adjusted under 35 U.S.C. 154(b) by 0 days.

(21) Appl. No.: 09/656,182

(22) Filed: Sep. 6, 2000

(51) Int. Cl.$^7$ .................................................. A61B 17/20
(52) U.S. Cl. .............................. 81/9.22; 606/186; 30/362
(58) Field of Search ................................ 81/9.22; 30/362, 30/366; 604/46, 47; 606/186, 116

(56) References Cited

U.S. PATENT DOCUMENTS

| | | |
|---|---|---|
| 498,519 | 5/1893 | Lewis et al. . |
| 635,814 | 10/1899 | Scott . |
| 768,413 | 8/1904 | Wagner . |
| 1,724,812 | 8/1929 | Waters . |
| 4,159,659 | 7/1979 | Nightingale . |
| 4,771,660 | 9/1988 | Yacowitz . |
| 5,054,339 | 10/1991 | Yacowitz . |
| 5,551,319 | 9/1996 | Spaulding et al. . |

FOREIGN PATENT DOCUMENTS

| | | |
|---|---|---|
| 690930 | 9/1930 | (FR) . |
| 13539 | 3/1900 | (GB) . |
| 1 587 519 | 4/1981 | (GB) . |

*Primary Examiner*—D. S. Meislin
(74) *Attorney, Agent, or Firm*—Richard C. Litman

(57) ABSTRACT

A contact bar assembly for a tattooing device having a spring saddle frame comprising an arcuate contact arm supporting a contact screw for making electrical contact with the contact spring. The proximate end of the contact arm is slotted for adjustment in a longitudinal direction. The distal end of the contact arm has a cylindrical lug disposed horizontally adapted to receive a cylindrical rod insert having a threaded axial bore. The lug has a pair of opposed slots for reception of the threaded contact screw, which also threads through the rod insert enabling adjustment of the contact screw in vertical or angular movement in the lug. The contact bar assembly is lightweight, balanced, and adjustment thereof is possible with the opposite free hand by either a right or left-handed tattooist.

5 Claims, 2 Drawing Sheets

CONTACT BAR ASSEMBLY FOR A TATTOOING DEVICE

BACKGROUND OF THE INVENTION

1. Field of the Invention

The present invention relates generally to an improvement for a tattooing device. More specifically, the invention is a contact bar assembly added to the spring saddle of a tattooing device.

2. Description of the Related Art

The related art of interest describes various tattooing devices, but none discloses the inclusion of a lightweight balanced contact bar assembly of the present invention. There is a need for a means to hold the contact screw above the contact point in a manner in which it can be readily adjusted forward, backward and vertically to enable the tattooing device to be virtually ambidextrous in adjustment during the operation.

The related art will be discussed in the order of perceived relevance to the present invention.

U.S. Pat. No. 4,159,659 issued on Jul. 3, 1979, to Carol Nightingale describes a tattooing device comprising a heavy frame including two electromagnetic coils, an armature assembly, and an interrupter switch inter alia. The interrupter switch has a wingnut which requires adjustment in its elongated slot at the top of the heavy frame. Therefore, adjustment of the wingnut position requires a left-handed tattooer to interrupt the tattooing process to make this adjustment. The tattooing device is distinguishable for its heavy frame and difficult adjustments for a left-handed tattooer.

U.S. Pat. No. 1,724,812 issued on Aug. 13, 1929, to Percy Waters describes an electric tattooing device which is unbalanced due to the standard 6 being on one side of the frame and requires adjustment of the lock screw on the binding post from one side. The device is distinguishable for its unbalanced structure and placement of the lock screw on one side.

U.S. Pat. No. 768,413 issued on Aug. 23, 1904, to Charles Wagner describes a tattooing device having its electromagnets arranged perpendicular to the longitudinal axis of the frame having a spiral spring connected to an arm and a switch lever on one side to cause some unbalance. There are two set screws on top for adjustment of the armature (connected to the needle) and the leaf spring contact. The device is distinguishable for its unbalanced structure and requirement for two set screws and a switch lever.

U.S. Pat. No. 498,519 issued on May 30, 1893, to Aaron D. Lewis et al. describes an electric perforating pen comprising a writing pen held by a pen holder on a handle containing a single electromagnet supported in a U-shaped bracket. A leaf spring contact screw assembly consists of a spring armature reed connected to an auxiliary leaf on the handle which supports the adjustable contact screw. The spring armature reed has a depressible portion and a perforating or indenting screw threadably insertable at its tip. The pen is distinguishable for its cantilevered two-leaf spring structure.

U.S. Pat. No. 4,771,660 issued on Sep. 20, 1988, and U.S. Pat. No. 5,054,339 issued on Oct. 8, 1991, to Harold Yacowitz describe a tattoo needle and holder assembly comprising a tubular holder having a continuous needle-supporting trough extending therethrough to its lower end, the trough being open to the user and readily adapted to receive a tattoo needle. A U-shaped frame placed on its side houses two electric coils and an extension of the needle holder which are held by elastic bands. The upper leg of the frame consists of a spring strip attached to an armature bar having a pin to hold the extension of the needle holder. The second patent adds a peristaltic pump actuated by a foot pedal. The assemblies are distinguishable for their single spring contact strip structures.

U.S. Pat. No. 5,551,319 issued on Sep. 3, 1996, to Darwin Spaulding et al. describes a variable speed controlled ink marking device having a D.C. motor and crank with an improved damping ability to prevent the needle from making unwanted movements of the needle in a plane perpendicular to the reciprocating motion. The damping is effected by a damping plate positioned between the motor and the mounting wall of the housing. A damping ring is positioned between the damping plate and the housing. This structural improvement removes undesirable movement of the needle. The device is distinguishable for its D.C. motor, crank structure and variable speed control.

U.S. Pat. No. 635,814 issued on Oct. 31, 1899, to Josiah Scott describes a stylus for producing illuminated sentences on a painted glass screen by producing arcs between a carbon point on a spring made from two strips separated by an asbestos layer. The spring is located on a rubber handle with a projecting carbon or metal strip. The stylus is distinguishable for its spring and handle structure.

French Pat. Application No. 690,930 published on Sep. 27, 1930, for Herbert Trau et al. describes an electric engraver apparatus comprising a housing for two coils, a single spring and battery. The housing is integrated with the needle and has an electric interrupter element on top. The apparatus is distinguishable for its single spring action.

British Pat. Application No. 13,539 published on Mar. 24, 1900, for Alfred C. South describes an improvement to a tattooing apparatus comprising a rectangular box housing having two coils, a hinged spring and armature element linked to the vertical needle. An external switch lever is positioned at an end opposite the needle. The apparatus is distinguishable for its single spring and switch levered structure.

British Pat. Application No. 1,587,519 published on Apr. 8, 1981, for Keith Langley describes a reciprocable tattooing instrument having a needle reciprocated by a cranked drive shaft with the ink supplied through the axial needle bore. The instrument is distinguishable for its crankshaft structure.

None of the above inventions and patents, taken either singularly or in combination, is seen to describe the instant invention as claimed. Thus, a contact bar assembly solving the aforementioned problems of unbalanced tattooing and heaviness is desired.

SUMMARY OF THE INVENTION

The present invention is directed to a contact bar assembly attached to a tattooing device having a spring saddle frame. The contact bar assembly comprises a contact bail arm supporting a contact screw for making electrical contact with the contact spring. This contact bar assembly can be extended forward, rearward and rotated in a vertical and axial motion relative to the contact spring for finer adjustment control of the contact spring. The contact bar assembly enables virtually ambidextrous operation of the tattooing device.

Accordingly, it is a principal object of the invention to provide a contact bar assembly attachable to a tattoo device.

It is another object of the invention to provide a contact bar assembly adjustable in two directions.

It is a further object of the invention to provide a contact bar assembly having a balanced weight distribution.

Still another object of the invention is to provide a contact bar assembly having the property of ambidextrous operation.

It is an object of the invention to provide improved elements and arrangements thereof for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT

Figure 1:
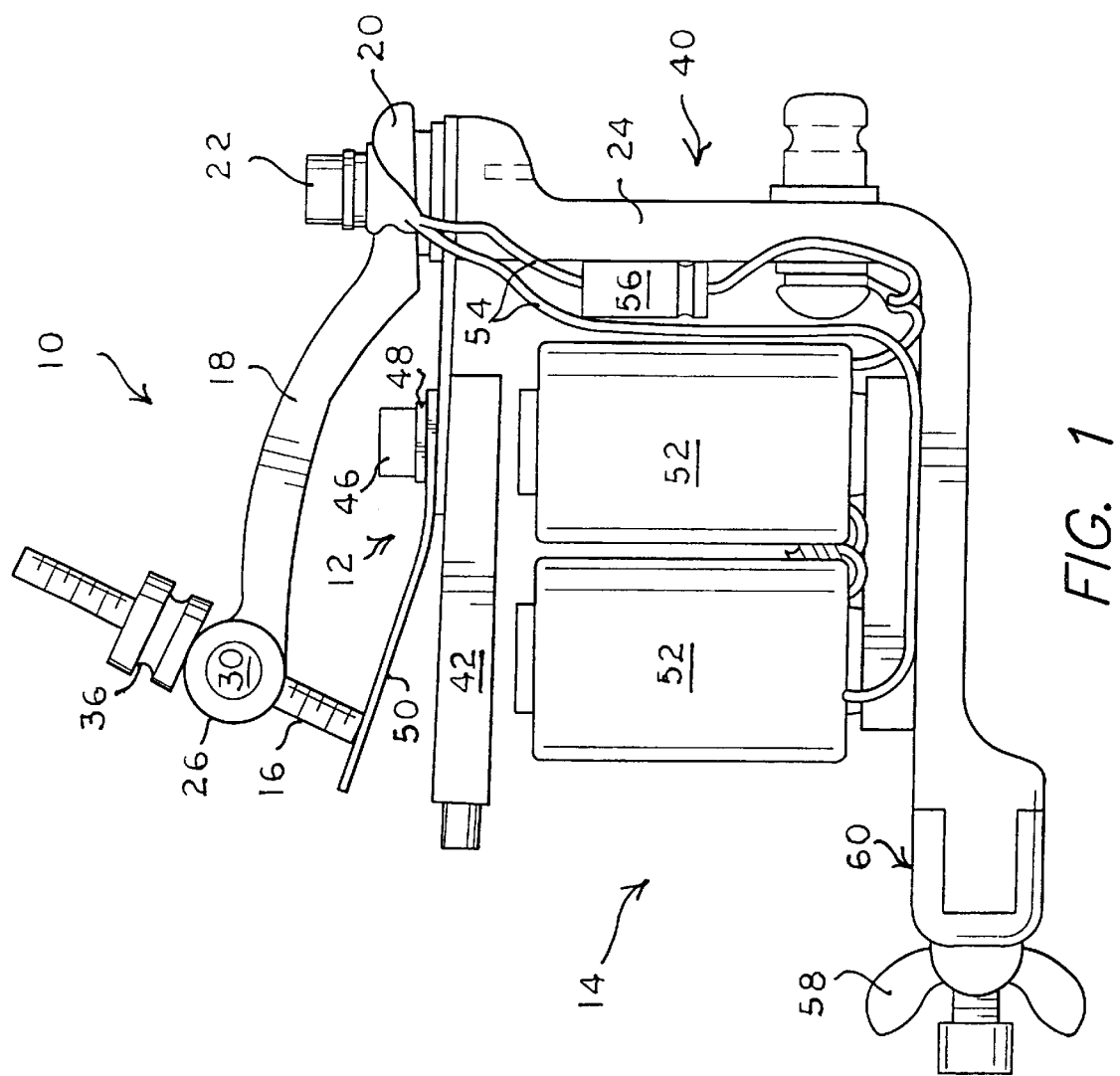
FIG. 1 is an environmental, perspective view of a contact bar assembly for a tattooing device according to the present invention.
Figure 2:
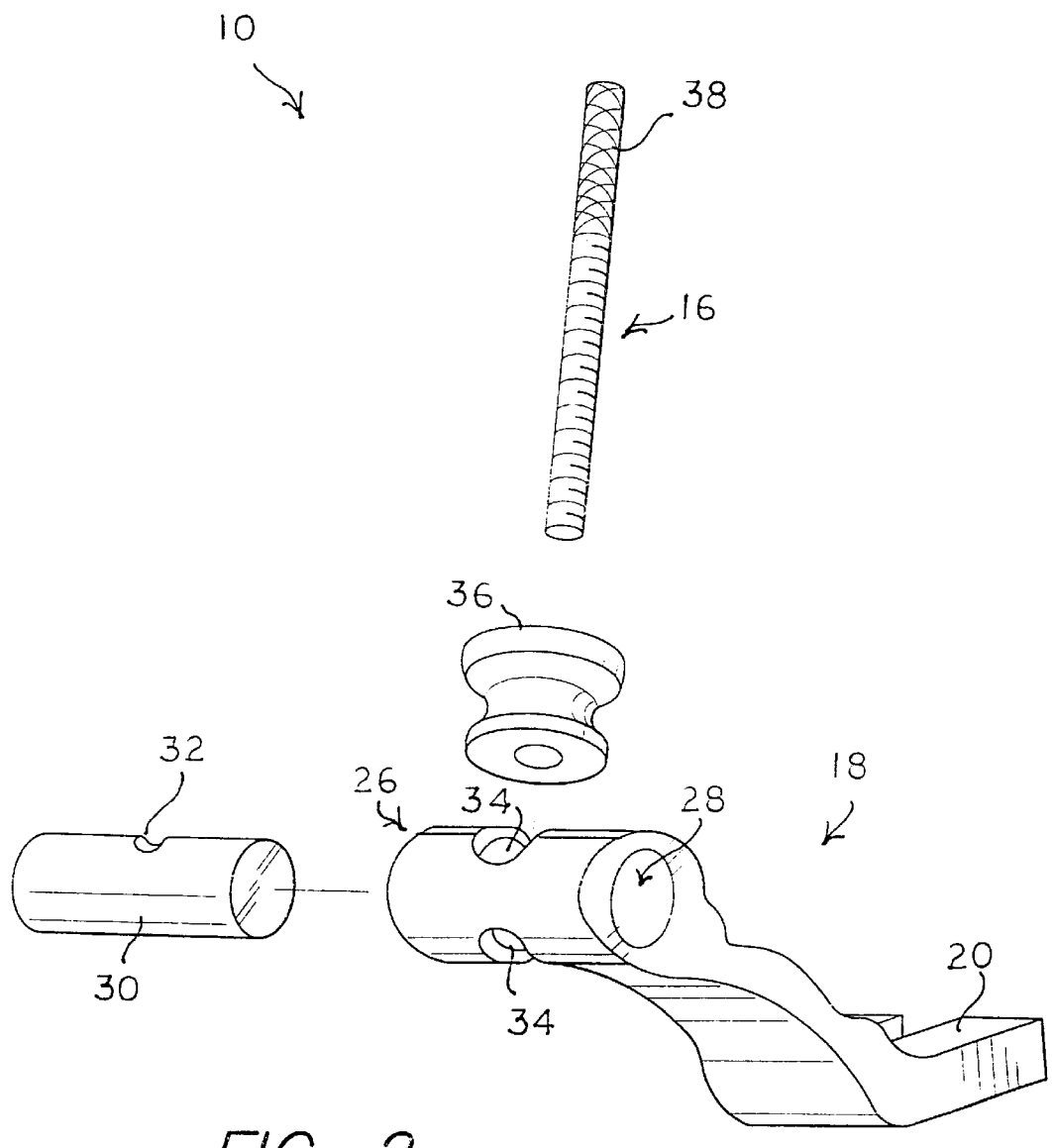
FIG. 2 is an exploded view of the contact bar assembly.

The present invention illustrated in FIGS. 1 and 2 is a contact bar assembly 10 mounted over the spring saddle 12 of a tattooing device 14 to provide a means to hold the contact screw 16 readily adjustable in height and inclination angle in the arm 18. The arm 18 has a forked proximate end 20 which is anchored by a socket cap screw 22 in the top of the rear standard 24 of the device 14. The forked end 20 provides a longitudinal adjustment of the arm 18 and consequently the contact screw vis-a-vis the spring saddle 12.

The arm 18 is arched upwards to end at its distal end in a horizontal lug 26 which has a horizontal throughbore 28 into which is inserted a friction-fitting cylindrical rod insert 30 coextensive in length with the throughbore 28. The rod insert 30 has a radial and threaded throughbore 32 which is aligned with two opposing axial slots 34 in the lug 26 for passage of the contact screw 16 therethrough. An externally grooved locknut 36 for improved manual adjustment is provided to secure the contact screw 16 in place on the lug 26. This structural arrangement permits an angular inclination of the contact screw 16 in the lug 26 adjustable by merely rotating the locknut 36 to loosen its grip on the lug 26, moving the position of the contact screw 16 in the slots 34, and retightening the locknut 36. The contact screw 16 has a knurled grip end 38 shown in FIG. 2 for movement up or down in the threaded rod insert 30.

It should be noted that the contact bar assembly 10 is positioned in a longitudinal direction of the tattooing device 14 and readily enables a right or left-handed artist to make adjustments with the opposite hand without switching the grip on the tattooing device 14.

Referring to FIG. 1, a conventional tattooing device 14 has a U-shaped bar housing 40 containing an armature bar 42 supported by a spring saddle 12 comprising a first contact spring 44 anchored at its proximate end by the socket cap screw 22 and a locking screw 46 and washer 48 at its distal end to also anchor the bent second contact spring 50. There are two in-line coils 52, requisite wiring 54, a capacitor 56, and a wingnut 58 for tightening the tube vise 60 holding the tattoo needle tube barrel and needle (not shown).

It is to be understood that the present invention is not limited to the embodiment described above, but encompasses any and all embodiments within the scope of the following claims.

I claim:

1. A contact bar assembly for a tattooing device comprising:
   an arcuate inclined arm having a longitudinal axis, a proximate end and a distal end;
   a slot formed in the proximate end of the arm for adjustment of the arm along its longitudinal axis on the tattooing device;
   a cylindrical lug formed at the arm distal end and perpendicular to the arm;
   said cylindrical lug having a horizontal throughbore and a pair of opposed axial slots perpendicular to said horizontal throughbore;
   a cylindrical rod having a centered threaded bore for frictional insertion into said horizontal throughbore of the cylindrical lug, for angular rotation of said rod; and
   an externally threaded contact screw for insertion into said opposed axial slots of the lug and the threaded bore of the cylindrical rod, for contact with a contact spring of the tattooing device;
   whereby the contact bar assembly is centrally balanced and the adjustment of the contact screw placement can be made with the opposite non-holding hand of a tattooist.

2. The contact bar assembly according to claim 1, wherein a socket screw cap fastens the proximate end of the arm to the tattooing device.

3. The contact bar assembly according to claim 1, wherein the contact screw has a knurled top end.

4. The contact bar assembly according to claim 1, further comprising contact screw height adjusting means, including the contact screw being adjusted in height in the arm from the contact spring by releasing the grooved locknut, rotating the contact screw and contacting the lug surface again with the grooved locknut.

5. The contact bar assembly according to claim 1, further comprising contact screw inclination angle adjusting means, including the contact screw being adjusted in an angle of inclination appropriate to contact the contact spring perpendicularly by rotating the rod insert.

\* \* \* \* \*